United States Patent
Kato et al.

(10) Patent No.: US 9,700,204 B2
(45) Date of Patent: Jul. 11, 2017

(54) OPHTHALMOLOGICAL DEVICE FOR MEASURING OCULAR DIMENSIONS

(71) Applicant: Tomey Corporation, Nagoya-shi, Aichi-ken (JP)

(72) Inventors: Chihiro Kato, Nagoya (JP); Yuji Nozawa, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 14/494,149

(22) Filed: Sep. 23, 2014

(65) Prior Publication Data

US 2015/0085256 A1 Mar. 26, 2015

(30) Foreign Application Priority Data

Sep. 24, 2013 (JP) ................................ 2013-197171

(51) Int. Cl.
- *A61B 3/117* (2006.01)
- *A61B 3/10* (2006.01)
- *A61B 3/00* (2006.01)

(52) U.S. Cl.
CPC ............ *A61B 3/117* (2013.01); *A61B 3/0008* (2013.01); *A61B 3/0025* (2013.01); *A61B 3/1005* (2013.01); *A61B 3/1173* (2013.01)

(58) Field of Classification Search
CPC ......... A61B 3/1225; A61B 3/12; A61B 3/103; A61B 3/1015; A61B 3/0008; A61B 3/102;

(Continued)

(56) References Cited

U.S. PATENT DOCUMENTS 5,396,303 A * 3/1995 Peters .................. A61B 3/12 351/211
5,491,524 A 2/1996 Hellmuth et al.
(Continued)

FOREIGN PATENT DOCUMENTS

EP 1602320 A1 12/2005
EP 2484273 A1 8/2012
(Continued)

OTHER PUBLICATIONS

European Search Report EP 14185961 dated Jan. 26, 2015 (6 pages).

*Primary Examiner* — Scott J Sugarman
*Assistant Examiner* — Henry Duong
(74) *Attorney, Agent, or Firm* — Shumaker, Loop & Kendrick, LLP

(57) ABSTRACT

An ophthalmological device emits light from a measurement optical system to an eye to be examined and calculates a dimension along the eye axis of a target portion of the eye from interfering light composed of reflected light from the eye and reference light. The measurement optical system includes incidence position changing member that changes the incidence position of light emitted to the eye, and driving unit that drives the incidence position changing member so as to scan at the incidence position of emitted light in a predetermined region of the eye. The predetermined region is a region where a straight line passes through when the straight line radially extended from the cornea apex of the eye is circumferentially moved over a predetermined angle range in the case of the eye is viewed from the front.

11 Claims, 7 Drawing Sheets

(58) Field of Classification Search
CPC ..... A61B 5/0066; A61B 3/117; A61B 3/0025; A61B 3/1173; A61B 3/1005; A61B 3/00–3/185; G01B 9/02091
USPC ......... 600/156; 250/252.1; 398/17; 351/200–247; 378/4; 356/451, 479, 491, 356/512
See application file for complete search history.

(56) References Cited

U.S. PATENT DOCUMENTS

| | | |
|---|---|---|
| 6,144,456 A | 11/2000 | Chavanne et al. |
| 2007/0002277 A1 | 1/2007 | Hanebuchi |
| 2007/0279592 A1 | 12/2007 | Hanebuchi |
| 2009/0149742 A1 | 6/2009 | Kato et al. |
| 2011/0292395 A1* | 12/2011 | Fercher ................ A61B 3/102 356/451 |
| 2012/0188511 A1* | 7/2012 | Kost ..................... A61B 3/107 351/211 |
| 2012/0200827 A1 | 8/2012 | Kato et al. |

FOREIGN PATENT DOCUMENTS

| | | |
|---|---|---|
| JP | H0515498 A | 1/1993 |
| JP | 2005-102938 A | 4/2005 |
| JP | 2005-348755 A | 12/2005 |
| JP | 2007-037984 A | 2/2007 |
| JP | 2007-313208 A | 12/2007 |
| JP | 2009-142313 A | 7/2009 |
| JP | 2012-161425 A | 8/2012 |
| WO | 2008/116270 A1 | 10/2008 |

\* cited by examiner

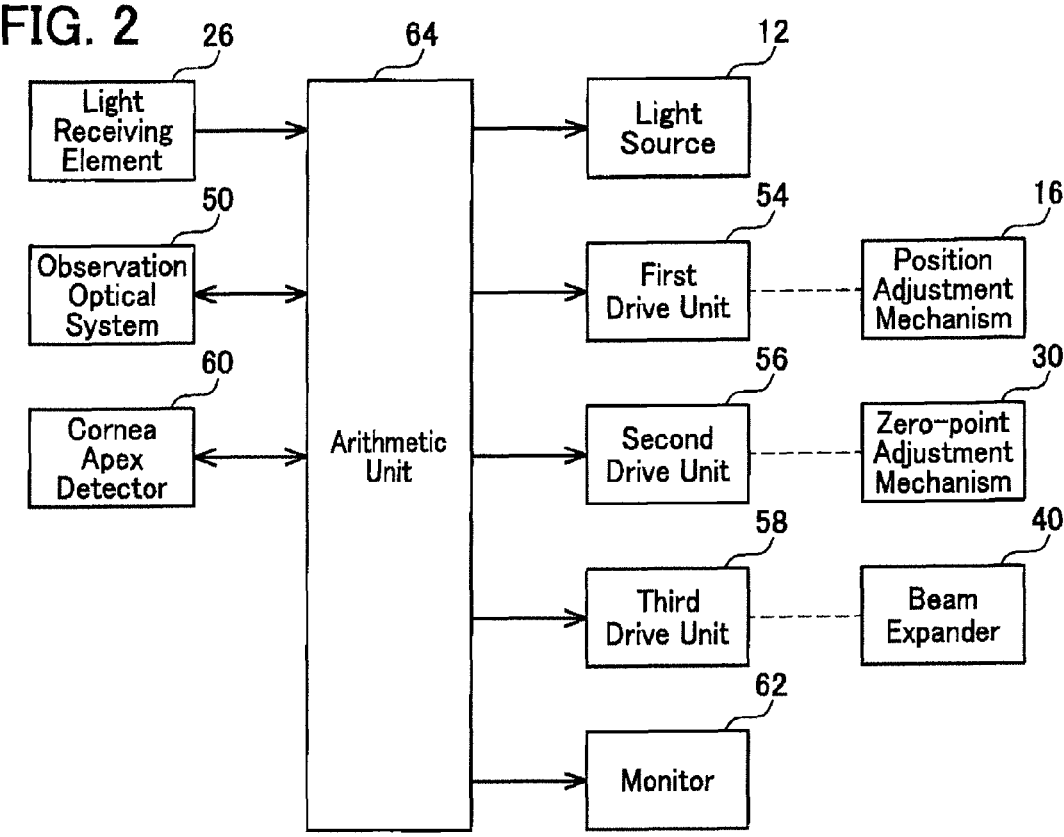
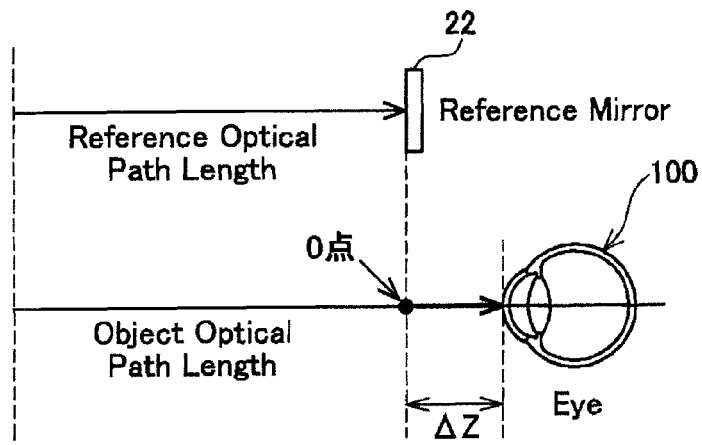

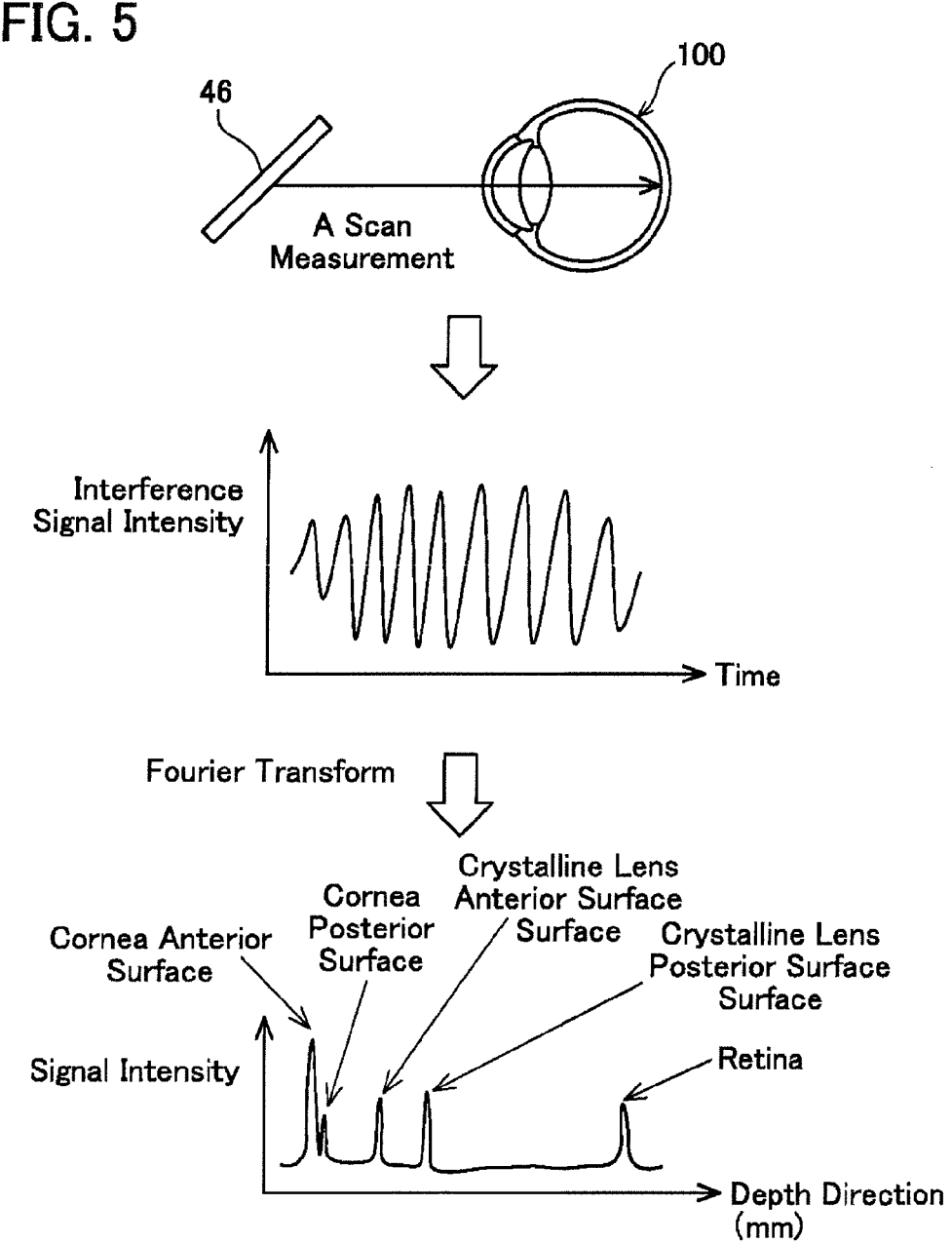

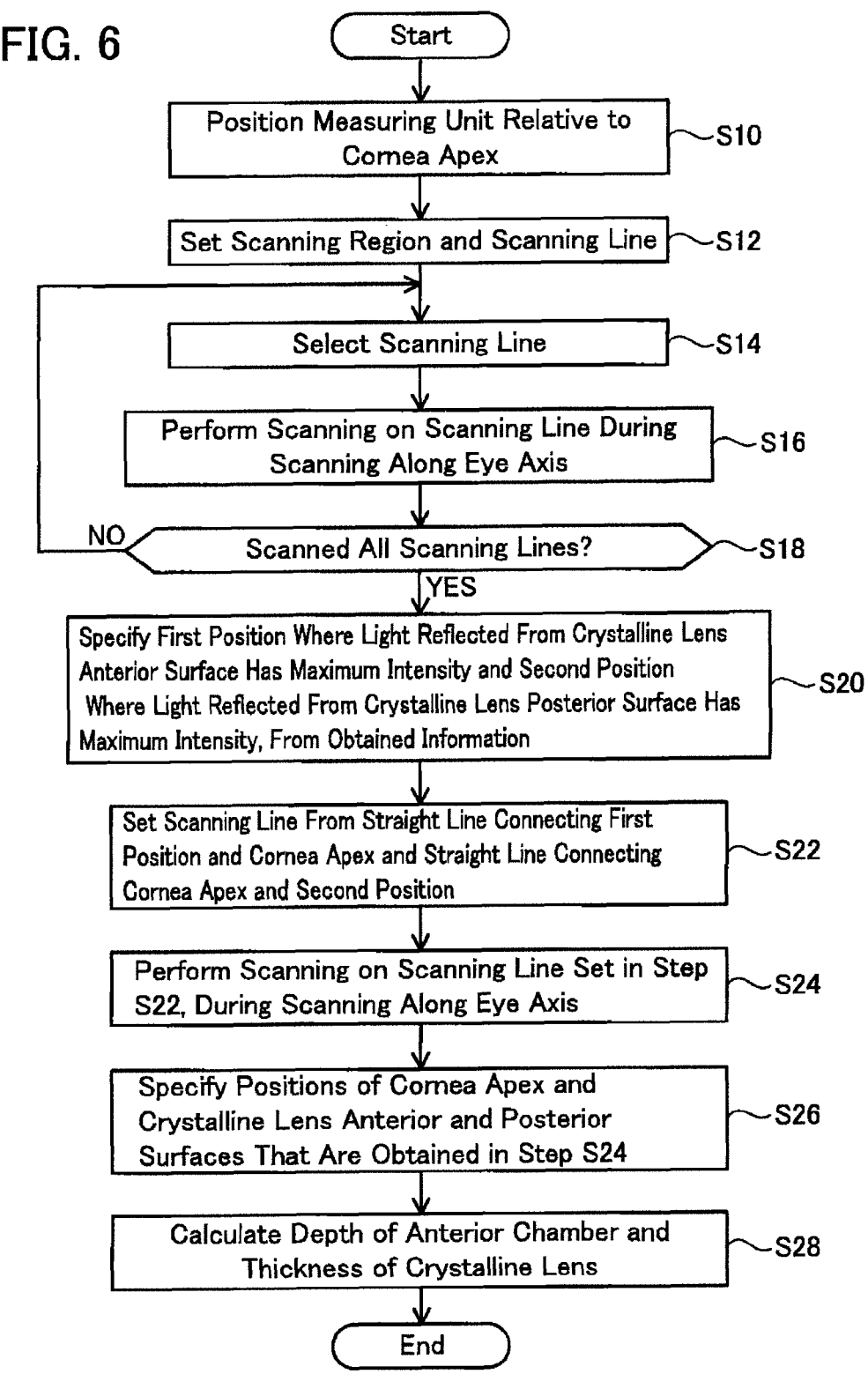

OPHTHALMOLOGICAL DEVICE FOR MEASURING OCULAR DIMENSIONS

CROSS-REFERENCE TO RELATED APPLICATION

This application claims priority to Japanese Patent Application No. 2013-197171 filed on Sep. 24, 2013, the contents of which are hereby incorporated by reference into the present application.

TECHNICAL FIELD

A technique disclosed in the present specification relates to an ophthalmological device for examining an eye to be examined, and particularly relates to an ophthalmological device for measuring the length (dimension) along the eye axis of a target portion (e.g., the depth of an anterior chamber and a crystalline lens) of an eye.

DESCRIPTION OF RELATED ART

An ophthalmological device under development measures a length (dimension) along the eye axis of a target portion (e.g., the depth of an anterior chamber and a crystalline lens) of an eye to be examined. Such an ophthalmological device includes a measurement optical system that emits light from a light source into an eye to be examined and guides reflected light, and a reference optical system that emits light from the light source to a reference surface and guides reflected light. Based on interfering light composed of reflected light that is guided by the measurement optical system and reflected light that is guided by the reference optical system, the anterior surface and the posterior surface of a target portion in the eye are located. When the anterior surface and the posterior surface of the target portion are located, a dimension along the eye axis (depth direction) of the target portion is calculated based on the positions of the anterior and posterior surfaces. Japanese Patent Application Publication No. 2007-37984 and Japanese Patent Application Publication No. 2007-313208 disclose conventional examples of such an ophthalmological device.

BRIEF SUMMARY OF INVENTION

In order to measure a dimension along the eye axis of a target portion, e.g., the depth of an anterior chamber and the thickness of a crystalline lens, it is necessary to receive light reflected from the anterior surface (front side) of the target portion and light reflected from the posterior surface (back side) of the target portion. In a conventional ophthalmological device, however, it is difficult to receive reflected light with sufficient intensity from both of the anterior and posterior surfaces of the target portion. Thus, a dimension along the eye axis of the target portion may not be calculated. For example, even if light is reflected with sufficient intensity from the anterior surface of the target portion so as to locate the anterior surface of the target portion, light reflected from the posterior surface of the target portion may not so intensive as to locate the posterior surface of the target portion. Alternatively, even if light is reflected with sufficient intensity from the posterior surface of the target portion, light may be reflected with insufficient intensity from the anterior surface of the target portion. In this case, a dimension of a target portion of an eye to be examined cannot be calculated along the eye axis. An object of the present teachings is to provide an ophthalmological device that can measure a dimension of a target portion of an eye to be examined with stability (high probability) along the eye axis.

An ophthalmological device disclosed in the present specification may include: a light source; a measurement optical system configured to emit light from the light source into an eye to be examined and guide reflected light; a reference optical system configured to split light from the light source and generate reference light; a light receiving element configured to receive interfering light composed of the reflected light guided by the measurement optical system and the reference light generated by the reference optical system; and an arithmetic unit configured to calculate a dimension along the eye axis of a target portion of the eye from interfering light received by the light receiving element. The measurement optical system may include: an incidence position changing member configured to change the incidence position of light emitted to the eye; and a driving unit configured to drive the incidence position changing member so as to scan at the incidence position of emitted light in a predetermined region of the eye. The predetermined region is a region where a straight line passes through when the straight line radially extended from the cornea apex of the eye is circumferentially moved over a predetermined angle range in the case of the eye is viewed from the front.

In the ophthalmological device, the incidence position changing member is driven by the driving unit so as to change the incidence position of light emitted to the eye and scan, in the predetermined region, the light emitted to the eye. A keen examination by the present inventors proved that when reflected light from the internal surfaces of the eye increases in intensity, a region having a predetermined positional relationship with the cornea apex of the eye is likely to contain the incidence position of light. Specifically, it is proved that reflected light is likely to increase in intensity when light is incident in a region circumferentially extended over a predetermined angle range relative to the cornea apex of an eye in front view. In the ophthalmological device, the predetermined region is the region circumferentially extended over the predetermined angle range relative to the cornea apex of the eye in front view, and light is scanned in the predetermined region. Thus, reflected light having sufficient intensity can be obtained from the internal surfaces of the eye with high probability, thereby stably specifying the positions of the internal surfaces of the eye.

BRIEF DESCRIPTION OF DRAWINGS

FIG. 2 is a block diagram showing the control system of the ophthalmological device according to the present embodiment.

FIG. 3 shows an explanatory drawing of the function of a zero-point adjustment mechanism.

FIG. 5 is an explanatory drawing showing the steps of processing an interference signal waveform obtained when the optical path length of a measurement optical system is scanned in a predetermined optical path length range.

FIG. 6 is a flowchart showing an example of the steps of the process of the ophthalmological device according to the present embodiment.

DETAILED DESCRIPTION OF INVENTION

Figure 1:
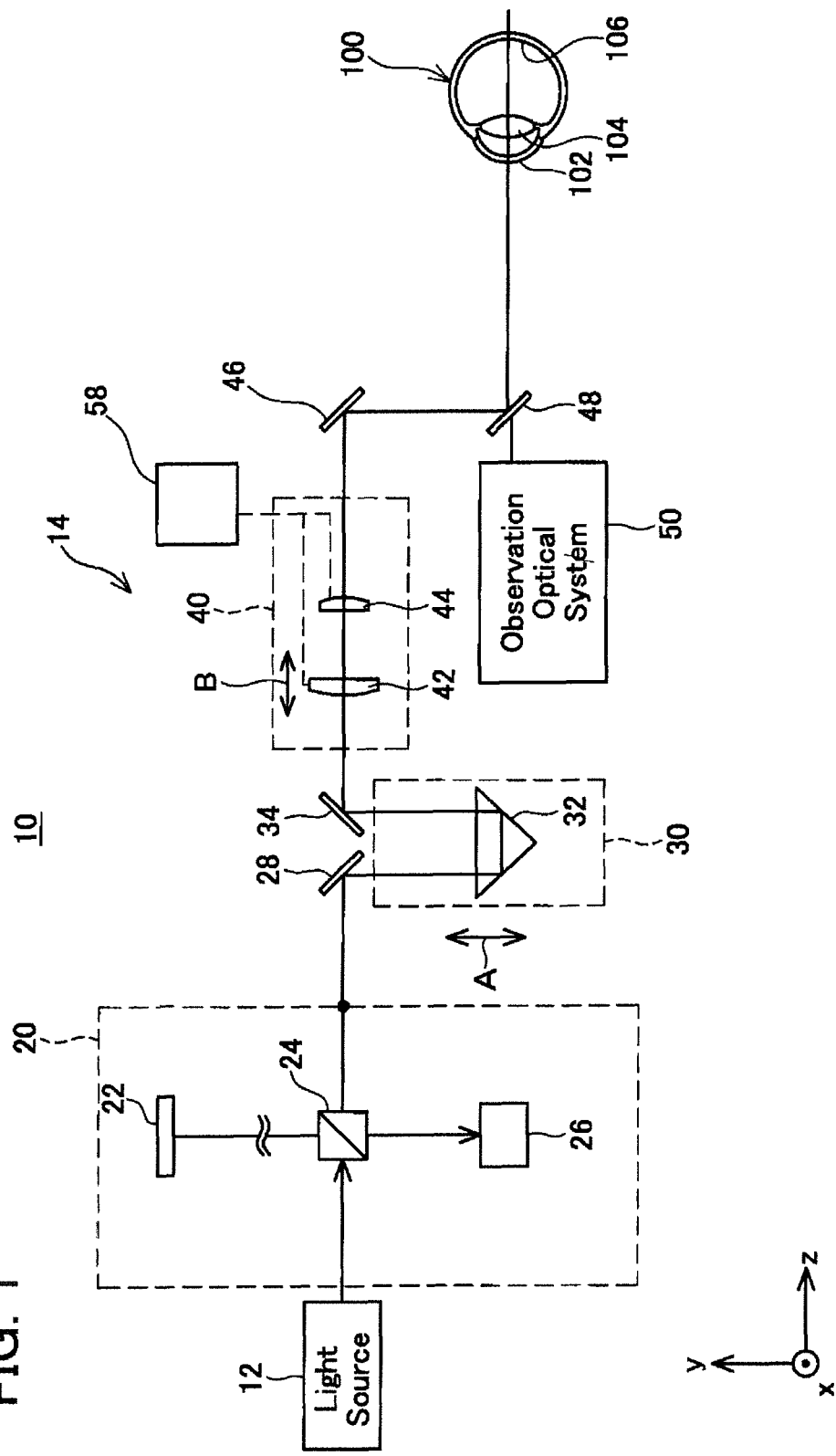
FIG. 1 is a schematic structural diagram showing the optical system of an ophthalmological device according to the present embodiment.

In an ophthalmological device disclosed in the present specification, an arithmetic unit may specify the position of the anterior surface of a target portion and the position of the posterior surface of the target portion from interfering light received when light emitted to an eye is scanned in a predetermined region, and the arithmetic unit may calculate a dimension along the eye axis of the target portion from the specified positions. With this configuration, the interfering light obtained by scanning light in the predetermined region is used so as to stably specify the positions of the anterior surface and the posterior surface of the target portion. This can stably calculate the dimension along the eye axis of the target portion.

In the ophthalmological device disclosed in the present specification, the incidence position at the acquisition of interfering light for specifying the position of the anterior surface of the target portion may be different from the incidence position at the acquisition of interfering light for specifying the position of the posterior surface of the target portion. With this configuration, the positions of the surfaces of the target portion are specified from reflected light obtained when light is incident at different positions of incidence of the eye. Thus, reflected light used for specifying the positions of the surfaces of the target portion can be sufficiently intensive. This can stably specify the positions of the surfaces of the target portion.

In the ophthalmological device disclosed in the present specification, when light emitted to the eye is scanned in the predetermined region, the arithmetic unit may specify a first incidence position where the intensity of light reflected from the anterior surface of the target portion is maximized and a second incidence position where the intensity of light reflected from the posterior surface of the target portion is maximized. In this case, a driving unit may further drive an incidence position changing member such that light emitted to the eye is scanned on a scanning line set so as to pass through the first incidence position and the second incidence position, and the arithmetic unit may calculate a dimension along the eye axis of the target portion from interfering light when light is scanned on the scanning line set so as to pass through the first incidence position and the second incidence position.

With this configuration, first, light emitted to the eye is scanned in the predetermined region, and then the first incidence position and the second incidence position are specified. Subsequently, light emitted to the eye is scanned on the scanning line passing through the first incidence position and the second incidence position. Thus, when light is scanned on the scanning line, reflected light with sufficient intensity can be received from the anterior surface of the target portion and reflected light with sufficient intensity can be received also from the posterior surface of the target portion. In other words, a thickness along the eye axis of the target portion can be calculated only by scanning, on the scanning line, light emitted to the eye. Since light emitted to the eye is scanned on the scanning line in a short time, the eye is placed in substantially the same state when the anterior surface of the target portion is specified and when the posterior surface of the target portion is specified. Thus, a dimension along the eye axis of the target portion can be calculated with high accuracy.

In the ophthalmological device disclosed in the present specification, when the eye is viewed from the front, one of the first and second incidence positions may be located on one side of a vertical line passing through the cornea apex of the eye, whereas the other incidence position may be located on the other side of the vertical line.

In the ophthalmological device disclosed in the present specification, the scanning line may include the cornea apex of the eye and have a first section connecting the cornea apex and the first incidence position and a second section connecting the cornea apex and the second incidence position. With this configuration, light emitted to the eye can be scanned from the first incidence position to the second incidence position through the cornea apex. Thus, the position of the cornea apex, the position of the anterior surface of the target portion, and the position of the posterior surface of the target portion can be obtained at the same time only by scanning light along the scanning line. Thus, dimensions along the eye axis can be accurately obtained. For example, if the target portion is a crystalline lens, the thickness of the crystalline lens (e.g., a dimension from the anterior surface to the posterior surface of the crystalline lens) and the depth of the anterior chamber (e.g., a dimension from the anterior surface or the posterior surface of a cornea to the anterior surface of the crystalline lens) can be obtained at the same time by setting the scanning line. In other words, scanning in the first section can obtain the positions of the anterior surface/posterior surface of the cornea and the anterior surface of the crystalline lens; meanwhile, scanning in the second section can obtain the positions of the anterior surface/posterior surface of the cornea and the posterior surface of the crystalline lens. Thus, the thickness of the crystalline lens and the depth of the anterior chamber can be obtained at the same time.

In the ophthalmological device disclosed in the present specification, when the eye is viewed from a front, the predetermined angle range is an angle range of +20° to +85° or −20° to −85° where (+) is a clockwise direction and (−) is a counterclockwise direction with respect to a reference line that is a vertical line extended upward from the cornea apex of the eye. As will be describe later, the above-mentioned angle range makes it possible to specify the positions of the posterior surface and the anterior surface of the crystalline lens of the eye with stability (high probability). The properly limited angle range allows a measurement of a length along the eye axis of the crystalline lens in a short time.

In the ophthalmological device disclosed in the present specification, the target portion may be the depth of the anterior chamber from the anterior surface or the posterior surface of the cornea to the anterior surface of the crystalline lens and/or the thickness of the crystalline lens from the anterior surface to the posterior surface of the crystalline lens. Since the normal direction of the crystalline lens is displaced from the optical axis of the eye, light is diagonally incident on the crystalline lens during measurements and the intensity of reflected light from the anterior surface and the posterior surface of the crystalline lens is likely to decrease. Hence, the use of the ophthalmological device described in the present specification can properly measure these portions.

In the ophthalmological device disclosed in the present specification, the incidence position changing member may be a lens disposed on the optical axis of light emitted to the eye. In this case, the driving unit may move the lens in a plane orthogonal to the optical axis. The use of the lens disposed on the optical axis can inexpensively perform two-dimensional scanning on light emitted to the eye. The lens used as the incidence position changing member may be, for example, one of lenses constituting a beam expander.

First Embodiment

As shown in FIG. 1, an ophthalmological device according to a first embodiment includes a measuring unit 10 for an examination of an eye 100. The measuring unit 10 includes a coherent optical system 14 that causes light reflected from the eye 100 and reference light to interfere with each other, an observation optical system 50 that observes an anterior eye part of the eye 100, and an alignment optical system (not shown) that aligns the measuring unit 10 with a predetermined positional relationship relative to the eye 100.

The coherent optical system 14 includes a light source 12, a measurement optical system that emits light from the light source 12 into the eye and guides reflected light, a reference optical system that emits light from the light source 12 to a reference surface and guides reflected light, and a light receiving element 26 that receives interfering light composed of reflected light that is guided by the measurement optical system and reference light guided by the reference optical system.

The light source 12 is a wavelength-swept (wavelength scanning) light source that changes the wavelength of emitted light with a predetermined period. In the present embodiment, the wavelength of light emitted from the light source 12 is changed; meanwhile, reflected light from an eye E and the reference light are caused to interfere with each other and interfering light is measured. Fourier transform on measured interfering light (interference signal) can specify the positions of interior portions (e.g., a crystalline lens and a retina) of the eye E. The light source 12 is a light source for emitting light with a wavelength of a 1-μm band (e.g., about 950 nm to 1100 nm).

The measurement optical system includes a beam splitter 24, a mirror 28, a zero-point adjustment mechanism 30, a mirror 34, a beam expander 40, a mirror 46, and a hot mirror 48. Light emitted from the light source 12 reaches the eye 100 through the beam splitter 24, the mirror 28, the zero-point adjustment mechanism 30, the mirror 34, the beam expander 40, the mirror 46, and the hot mirror 48. Reflected light from the eye 100 is guided to the light receiving element 26 through the hot mirror 48, the mirror 46, the beam expander 40, the mirror 34, the zero-point adjustment mechanism 30, the mirror 28, and the beam splitter 24. The zero-point adjustment mechanism 30 and the beam expander 40 will be specifically described later.

The reference optical system includes the beam splitter 24 and a reference mirror 22. Emitted from the light source 12 is partially reflected by the beam splitter 24, is emitted to the reference mirror 22, and then is reflected by the reference mirror 22. Light reflected by the reference mirror 22 is guided to a light receiving element 26 through the beam splitter 24. The reference mirror 22, the beam splitter 24, and the light receiving element 26 are disposed at fixed positions in an interferometer 20. Thus, in the ophthalmological device of the present embodiment, the reference optical path length of the reference optical system is kept constant.

The light receiving element 26 detects interfering light composed of light guided by the reference optical system and light guided by the measurement optical system. The light receiving element 26 may be, for example, a photodiode.

The observation optical system 50 emits observation light to the eye 100 through the hot mirror 48 and takes an image of light reflected from the eye 100 (that is, reflected light of emitted observation light). In this case, the hot mirror 48 transmits light from the light source of the observation optical system while reflecting light from the light source 12 of the coherent optical system. Thus, the ophthalmological device of the present embodiment can simultaneously makes a measurement using the coherent optical system and an observation of an anterior eye part by means of the observation optical system 50. The observation optical system 50 may be an optical system used for a known ophthalmological device and thus the explanation thereof is omitted.

The zero-point adjustment mechanism 30 and the beam expander 40 that are provided in the measurement optical system will be described below. The zero-point adjustment mechanism 30 includes a corner cube 32 and a second drive unit 56 (shown in FIG. 2) that moves the corner cube 32 forward and backward relative to the mirrors 28 and 34. The second drive unit 56 drives the corner cube 32 along an arrow A in FIG. 1 so as to change an optical path length from the light source 12 to the eye 100 (that is, the object optical path length of the measurement optical system). As shown in FIG. 3, in the case of an optical path difference Δz between an object optical path length from the light source 12 to the detection surface (a cornea surface in FIG. 3) of the eye 100 (specifically, the light source 12 to the detection surface+the detection surface to the light receiving element 26) and a reference optical path length from the light source 12 to the reference mirror 22 (specifically, the light source 12 to the reference mirror 22+the reference mirror 22 to the light receiving element 26), the intensity of interfering light composed of light reflected from the detection surface and the reference light decreases as the optical path difference Δz increases. Conversely, as the optical path difference Δz decreases, the intensity of interfering light increases. Thus, in the present embodiment, the object optical path length is changed by the zero-point adjustment mechanism 30, thereby changing a position where the reference optical path length matches the object optical path length (so-called zero point) from the surface of a cornea 102 to the surface of a retina 106.

The beam expander 40 includes a convex lens 42 disposed closer to the light source 12, a convex lens 44 disposed closer to the eye 100, and a third drive unit 58 that moves forward and backward the convex lens 42 along an optical axis (z-axis) relative to the convex lens 44 and moves the convex lens 44 in a plane (xy plane) orthogonal to the optical axis. The convex lens 42 and the convex lens 44 are disposed on the optical axis and changes the focal position of incoming parallel light. In other words, the third drive unit 58 moves the convex lens 42 along an arrow B in FIG. 1. Thus, the focal position of light emitted to the eye 100 changes in the depth direction of the eye 100. Specifically, in a state in which a distance between the convex lens 42 and the convex lens 44 is adjusted so as to emit parallel light from the convex lens 44, the convex lens 42 is moved in a direction that separates from the convex lens 44, the light emitted from the convex lens 44 is converged. If the convex lens 42 is moved in a direction that approaches the convex lens 44, light emitted from the convex lens 44 is diverged. This allows the focal position of light emitted to the eye 100 to coincide with the surface of the cornea 102 or the surface of the retina 106 of the eye 100. Thus, the intensity of light reflected from the surfaces of the cornea 102 and the retina 106 can be increased so as to precisely detect the positions of the surfaces.

The convex lens 44 can be two-dimensionally moved in the plane (xy plane) orthogonal to the optical axis relative to the convex lens 42. In other words, the third drive unit 58 two-dimensionally drives the convex lens 44 in the plane (xy plane) orthogonal to the optical axis relative to the convex lens 42. Thus, the incidence position of light from the light source 12 to the eye 100 two-dimensionally changes relative to the eye 100. Specifically, in FIG. 4, a plan view of the eye 100, the incidence position two-dimensionally changes in the plane (xy plane). For example, if the convex lens 44 is moved in y direction relative to the convex lens 42, the incidence position also changes in y direction. Furthermore, the convex lens 44 moved in x direction relative to the convex lens 42 changes the incidence position in x direction. Thus, the convex lens 44 moved in x direction and/or y direction relative to the convex lens 42 changes the incidence position in the xy plane.

In the beam expander 40 of the present embodiment, the convex lens 42 is moved along the optical axis so as to adjust the focal position of light, and the convex lens 44 is moved in the plane orthogonal to the optical axis so as to adjust the incidence position of light. The present teachings is not limited to this configuration. For example, the focal position of light may be changed by moving the convex lens 44 instead of the convex lens 42 along the optical axis. The convex lens 42 may be moved instead of the convex lens 44 in the plane orthogonal to the optical axis so as to adjust the incidence position of light. Alternatively, the focal position of light and the incidence position of light may be adjusted by moving one of the convex lens 42 and the convex lens 44 along the optical axis and in the plane orthogonal to the optical axis relative to the other lens. In the present embodiment, the beam expander 40 includes the two convex lenses 42 and 44. The beam expander may include three or more lenses. For example, the convex lens 42 may include a plurality of lenses.

Figure 4A:
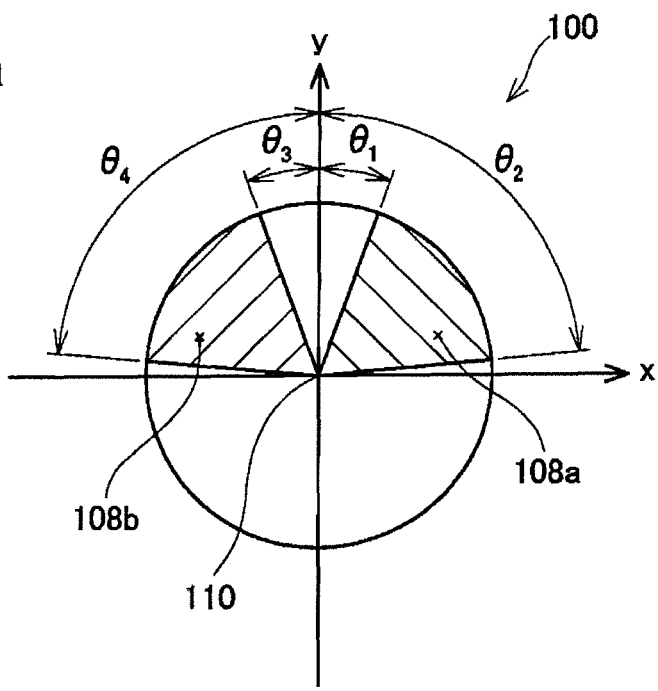
FIGS. 4a and 4b show explanatory drawings of predetermined regions for scanning light from a light source and scanning lines set in the predetermined regions.

As shown in FIG. 4, in the present embodiment, the third drive unit 58 drives the convex lens 44 such that the incidence position of light emitted to the eye 100 is scanned in predetermined regions 108$a$ and 108$b$. The predetermined region 108$a$ is a sector region extended over an angle range of $\theta 1$ to $\theta 2$ in a circumferential direction (clockwise direction) with respect to a reference line that is a perpendicular line (y axis in FIGS. 4($a$) and 4($b$)) extended upward from a cornea apex 110 of the eye 100. The predetermined region 108$b$ is a sector region extended over an angle range of $\theta 3$ to $\theta 4$ in a circumferential direction (counterclockwise direction) with respect to the reference line (y axis). As has been discussed, the predetermined regions 108$a$ and 108$b$ may be regions where a straight line passes through when the straight line radially extended from the cornea apex 110 of the eye 100 is circumferentially moved over the angle range of $\theta 1$ to $\theta 2$ or $\theta 3$ to $\theta 4$ in the case of the eye 100 is viewed from the front. The dimensions of the predetermined regions 108$a$ and 108$b$ in radial directions (that is, the lengths of the straight lines) may be each set at a predetermined length (e.g., about 1 mm to 3 mm) from the cornea apex.

As shown in experimental results (see FIGS. 7 and 8), if the eye 100 is a right eye, light reflected from the anterior surface of the crystalline lens 104 has maximum intensity when the incidence position is located in the region 108$a$, whereas light reflected from the posterior surface of the crystalline lens 104 has maximum intensity when the incidence position is located in the region 108$b$. If the eye 100 is a left eye, light reflected from the posterior surface of the crystalline lens 104 has maximum intensity when the incidence position is located in the region 108$a$, whereas light reflected from the anterior surface of the crystalline lens 104 has maximum intensity when the incidence position is located in the region 108$b$. Thus, by scanning the incidence position of light emitted to the eye 100 in the predetermined regions 108$a$ and 108$b$, the incidence position of light can be efficiently specified at the maximum intensity of reflected light from the anterior surface and the posterior surface of the crystalline lens 104. In the present embodiment, $\theta 1$ is +20°, $\theta 2$ is +85°, $\theta 3$ is −20°, and $\theta 4$ is −85°. In this case, (+) denotes a clockwise direction while (−) denotes a counterclockwise direction.

In the present embodiment, a plurality of scanning lines 112 are set in the predetermined regions 108$a$ and 108$b$ so as to cover the predetermined regions 108$a$ and 108$b$ (only one of the scanning lines 112 is shown in FIG. 4($b$)). As shown in FIG. 4($b$), the scanning line 112 is composed of a linear part extended from the cornea apex 110 in the predetermined region 108$b$ and a linear part extended from the cornea apex in the predetermined region 108$a$. The scanning line 112 is a straight line passing through the cornea apex 110 and thus line can be completely scanned over the predetermined regions 108$a$ and 108$b$.

The alignment optical system may be an optical system used for a known ophthalmological device. The alignment optical system includes a detector 60 (shown in FIG. 2) that detects the position of the cornea apex 110 of the eye 100. In the present embodiment, the cornea apex detector 60 detects the cornea apex 110 of the eye 100, and then the position of the measuring unit 10 (specifically, the optical system other than the interferometer 20 in the measuring unit 10) is adjusted based on the detection result. This locates the measuring unit 10 at a predetermined position relative to the cornea apex 110 of the eye 100. The ophthalmological device of the present embodiment includes, as mechanisms for adjusting the position of the measuring unit 10, a position adjustment mechanism 16 (shown in FIG. 2) for adjusting the position of the measuring unit 10 relative to the eye 100 and a first drive unit 54 (shown in FIG. 2) for driving the position adjustment mechanism 16. The alignment optical system and the cornea apex detector 60 can have known configurations and thus the detailed explanation thereof is omitted.

The configuration of the control system of the ophthalmological device according to the present embodiment will be described below. As shown in FIG. 2, the ophthalmological device is controlled by an arithmetic unit 64. The arithmetic unit 64 includes a microcomputer (microprocessor) having a CPU, a ROM, a RAM, and so on. The arithmetic unit 64 is connected to the light source 12, the first to third drive units 54 to 58, a monitor 62, and the observation optical system 50. The arithmetic unit 64 controls on/off of the light source 12, controls the first to third drive units 54 to 58 so as to drive the mechanisms 16, 30, and 40, and controls the observation optical system 50 to display an anterior eye part image, which is captured by the observation optical system 50, on the monitor 62. The arithmetic unit 64 is connected to the light receiving element 26 and receives the interference signal corresponding to the intensity of interfering light detected by the light receiving element 26. The arithmetic unit 64 performs Fourier transform on the interference signal from the light receiving element 26 so as to specify the positions of the parts of the eye 100 (the anterior and posterior surfaces of the cornea 102, the anterior and posterior faces of the crystalline lens 104, and the surface of the retina 106), and calculates a dimension (e.g., the depth of an anterior chamber and the thickness of a crystalline lens) along an eye axis of the eye 100. The arithmetic unit 64 is connected to the cornea apex detector 60 and receives a signal from the cornea apex detector 60. The arithmetic unit 64 drives the position adjustment mechanism 16 by means of the first drive unit 54 based on the signal from the cornea apex detector 60. Processing for specifying the positions of the parts of the eye 100 by means of the arithmetic unit 64 will be specifically described later.

The following will discuss the steps of measuring the thickness (a dimension from the anterior surface to the posterior surface of the crystalline lens 104) and the depth of the anterior chamber (a dimension from the anterior surface or posterior surface of the cornea 102 to the anterior surface of the crystalline lens 104) of the crystalline lens 104 by means of the ophthalmological device of the present embodiment. As shown in FIG. 6, first, an examiner operates a switch (a switch for inputting the start of measurement, not shown). At this point, the arithmetic unit 64 positions the measuring unit 10 based on the position of the apex of the cornea 102 detected by the cornea apex detector 60 (S10). In other words, the arithmetic unit 64 processes the signal from the cornea apex detector 60 so as to specify the position of the apex of the cornea 102 of the eye 100. Moreover, the arithmetic unit 64 drives the position adjustment mechanism 16 by means of the first drive unit 54 to position the measuring unit 14 such that the apex of the cornea 102 of the eye 100 is located on the optical axis of the measurement optical system. This adjusts the positions of the measuring unit 10 in xy direction (vertical and horizontal directions) and z direction (forward or backward direction) relative to the eye 100. The positioning of the measuring unit 14 locates the apex of the cornea 102 at the center of an anterior eye part image captured by the observation optical system 50. Moreover, the arithmetic unit 64 drives the second and third drive units 56 and 58 to adjust the zero-point adjustment mechanism 30 and the beam expander 40. Thus, the focus of light emitted from the light source 12 to the eye 100 is located at a predetermined position of the eye 100 (e.g., the anterior surface of the crystalline lens 104). Moreover, the zero point where an object optical path length matches a reference optical path length is disposed at a predetermined position of the eye 100 (e.g., the anterior surface of the crystalline lens 104). In step S10, the convex lens 44 of the beam expander 40 is driven only along the optical axis.

Subsequently, the arithmetic unit 64 sets the light emission region of the eye 100 (the predetermined regions 108a and 108b in FIG. 4) and sets the scanning lines (the scanning line 112 in FIG. 4) in the predetermined regions (S12). Specifically, in the ophthalmological device of the present embodiment, the predetermined regions 108a and 108b (θ1 to θ2, θ3 to θ4) corresponding to measured portions are stored in the memory of the arithmetic unit 64. Thus, the arithmetic unit 64 reads the predetermined regions 108a and 108b from the memory according to the measured portions. Subsequently, the arithmetic unit 64 sets the scanning lines 112 in the predetermined regions 108a and 108b so as to emit light over the predetermined regions 108a and 108b. In other words, all the scanning lines 112 are scanned with light from the light source 12, leading to light emission over the predetermined regions 108a and 108b from the light source. This can obtain tomographic information on the overall predetermined regions 108a and 108b.

At the completion of the settings of the predetermined regions 108a and 108b and the scanning line 112, the arithmetic unit 64 selects one of the set scanning lines 112 (S14). Subsequently, the arithmetic unit 64 changes the frequency of light emitted from the light source 12; meanwhile, the arithmetic unit 64 drives the beam expander 40 by means of the third drive unit 58 such that the incidence position of light to the eye 100 from the light source 12 moves on the scanning line (S16). At this point, the arithmetic unit 64 processes the interference signal inputted from the light receiving element 26, thereby obtaining two-dimensional tomographic information at the position of the scanning line selected in step S14. Specifically, as has been discussed, when the frequency of light emitted from the light source 12 is changed, a position where the measuring light and the reference light interfere with each other to generate interference waves is changed in the depth direction of the eye 100. Thus, as shown in FIG. 5, the interference signal outputted from the light receiving element 26 changes in signal intensity with time. This signal is generated by interference waves of reflected light from the parts of the eye 100 (the anterior and posterior surfaces of the cornea 102, the anterior and posterior faces of the crystalline lens 104, and the surface of the retina 106) and the reference light. Thus, the arithmetic unit 64 performs Fourier transform on the signal inputted from the light receiving element 26. This separates, from the signal, interference signal components of light reflected from the parts (the anterior and posterior surfaces of the cornea 102, the anterior and posterior surfaces of the crystalline lens 104, and the surface of the retina 106) of the eye 100. Hence, the arithmetic unit 64 can specify the positions of the parts of the eye 100. During the processing, the scanning line 112 is scanned with light from the light source 12. In other words, the arithmetic unit 64 drives the beam expander 40 by means of the third drive unit 58 (specifically, the convex lens 44 is driven in a plane orthogonal to the optical axis) so as to move the incidence position of light on the scanning line. This allows the arithmetic unit 64 to obtain two-dimensional tomographic information corresponding to the position of the scanning line 112. As described above, the intensity of light reflected from the parts of the eye 100 changes depending on the incidence position of light. Thus, the two-dimensional tomographic information obtained by scanning on the scanning line 112 may not specify the positions of the parts of the eye 100 because reflected light from the parts of the eye 100 varies in intensity depending on the incidence position.

Subsequently, the arithmetic unit 64 decides if all the scanning lines 112 set in step S12 have been measured as in step S16 (S18). If all the scanning lines have not been measured as in step S16 (NO in step S18), the process returns to step S14 to repeat processing from step S14. This obtains two-dimensional tomographic information at positions corresponding to all the scanning lines 112 set in step S12.

If the measurement of step S16 is conducted on all the scanning lines (YES in step S18), the arithmetic unit 64 specifies, from the two-dimensional tomographic information on the scanning lines, the incidence position of light (hereinafter, will be called a first position) when light reflected from the anterior surface position of the crystalline lens 104 of the eye 100 has maximum intensity, and the incidence position of light (hereinafter, will be called a second position) when light reflected from the posterior surface position of the crystalline lens 104 of the eye 100 has maximum intensity (S20). As described above, light reflected from the parts of the eye 100 changes depending on the incidence position of light to the eye 100. Thus, the interference signal obtained in light emission at an incidence position is subjected to Fourier transform so as to separate the interference signal components of light reflected from the parts (the anterior and posterior surfaces of the cornea 102, the anterior and posterior surfaces of the crystalline lens 104, and the surface of the retina 106) of the eye 100 at the same position. The intensity of the interference signal component varies depending on the intensity of light reflected from the corresponding surface. Thus, the arithmetic unit 64 decides an incidence position where the interference signal component corresponding to the anterior surface position of the crystalline lens 104 is maximized. The incidence position where the interference signal component is maximized will be referred to as "first incidence position". Similarly, the arithmetic unit 64 decides an incidence position where the interference signal component corresponding to the posterior surface of the crystalline lens 104 is maximized. The incidence position where the interference signal component is maximized will be referred to as "second incidence position".

Figure 4B:
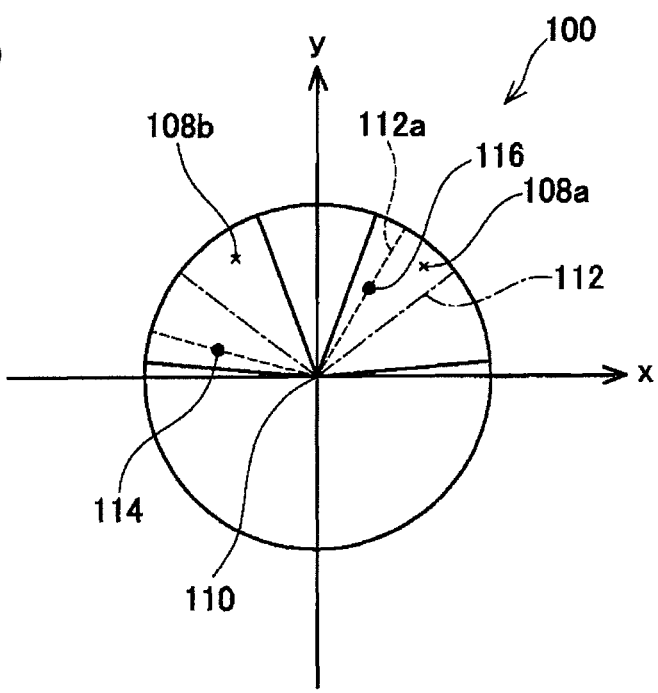

Subsequently, the arithmetic unit 64 connects a straight line that connects "first incidence position" specified in step S20 and the cornea apex and a straight line that connects "second incidence position" specified in step S20 and the cornea apex, setting another scanning line (S22). For example, as shown in FIG. 4(b), a first incidence position 114 is specified in the predetermined region 108b while a second incidence position 116 is specified in the predetermined region 108a. In this case, a scanning line 112a is set as another scanning line including a straight line connecting the first incidence position 114 and the cornea apex 110 and a straight line connecting the second incidence position 116 and the cornea apex 110.

When another scanning line 112a is set, the arithmetic unit 64 drives the beam expander 40 by means of the third drive unit 58 such that the incidence position of light from the light source 12 to the eye 100 moves on the scanning line 112a while the frequency of light emitted from the light source 12 is changed (S24). The scanning line 112a includes "first incidence position" where the intensity of light reflected from the anterior surface of the crystalline lens 104 is maximized and "second incidence position" where light reflected from the posterior surface of the crystalline lens 104 is maximized. When light from the light source 12 is incident on the apex of the cornea 102, reflected light from the anterior and posterior surfaces of the cornea 102 has the maximum intensity. Thus, the interference signal obtained in step S24 includes an interference signal component that is sufficiently intensive to specify the positions of the anterior and posterior surfaces of the cornea 102, an interference signal component that is sufficiently intensive to specify the position of the anterior surface of the crystalline lens 104, and an interference signal component that is sufficiently intensive to specify the position of the posterior surface of the crystalline lens 104. These interference signal components are obtained during scanning of a scanning line. In other words, the interference signal is obtained in quite a short time and thus these interference signal components can be obtained while the eye 100 is substantially kept in a constant state.

When the interference signal is obtained in step S24, the arithmetic unit 64 specifies the position of the anterior surface of the crystalline lens 104 from the interference signal, specifies the position of the posterior surface of the crystalline lens 104, and specifies the position of the anterior or posterior surface of the cornea 102 (S26). As described above, the interference signal obtained in step S24 includes the interference signal component that is sufficiently intensive to specify the position of the anterior surface of the crystalline lens 104, the interference signal component that is sufficiently intensive to specify the position of the posterior surface of the crystalline lens 104, and the interference signal component that is sufficiently intensive to specify the positions of the anterior and posterior surfaces of the cornea 102. Since the interference signal is obtained in quite a short time in step S24, the eye 100 is kept in substantially a constant state. Thus, the arithmetic unit 64 can precisely specify the position of the anterior surface of the crystalline lens 104, the position of the posterior surface of the crystalline lens 104, and the positions of the anterior and posterior surfaces of the cornea 102. When these positions are specified, the arithmetic unit 64 calculates the thickness of the crystalline lens 104 of the eye 100 (a dimension from the anterior surface to the posterior surface of the crystalline lens 104) and the depth of the anterior chamber (a dimension from the anterior surface or posterior surface of the cornea 102 to the position of the anterior surface of the crystalline lens 104) (S28). The calculated value is displayed on the monitor 62. As described above, the positions of the anterior and posterior surfaces of the crystalline lens 104 and the positions of the anterior and posterior surfaces of the cornea 102 are specified with high accuracy, thereby accurately calculating the thickness and the depth of the anterior chamber of the crystalline lens 104.

Figure 7:
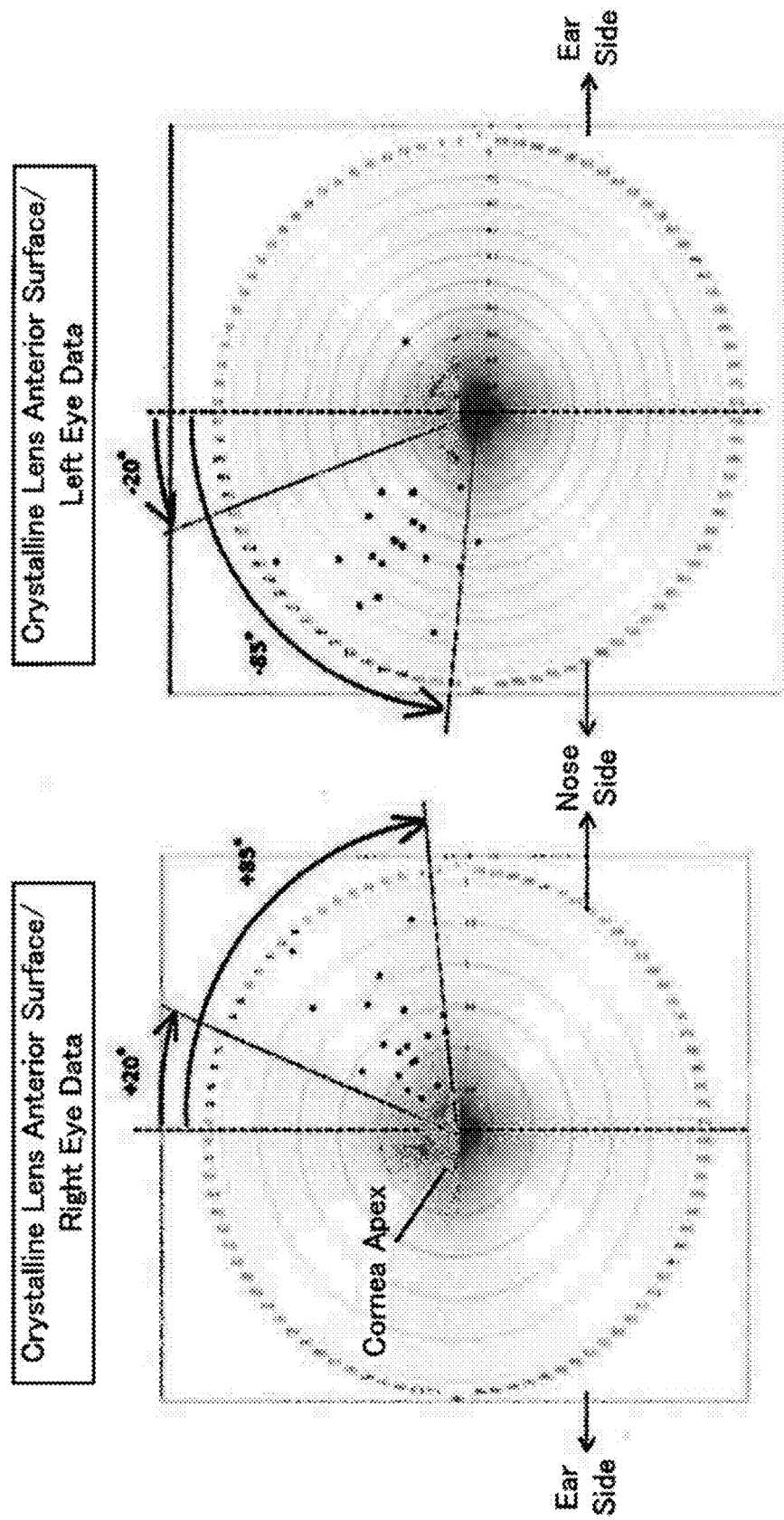
FIG. 7 shows experimental results when the positions of incidence are determined by experiments so as to maximize the intensity of reflected light from the anterior surface of a crystalline lens (right eye, left eye).
Figure 8:
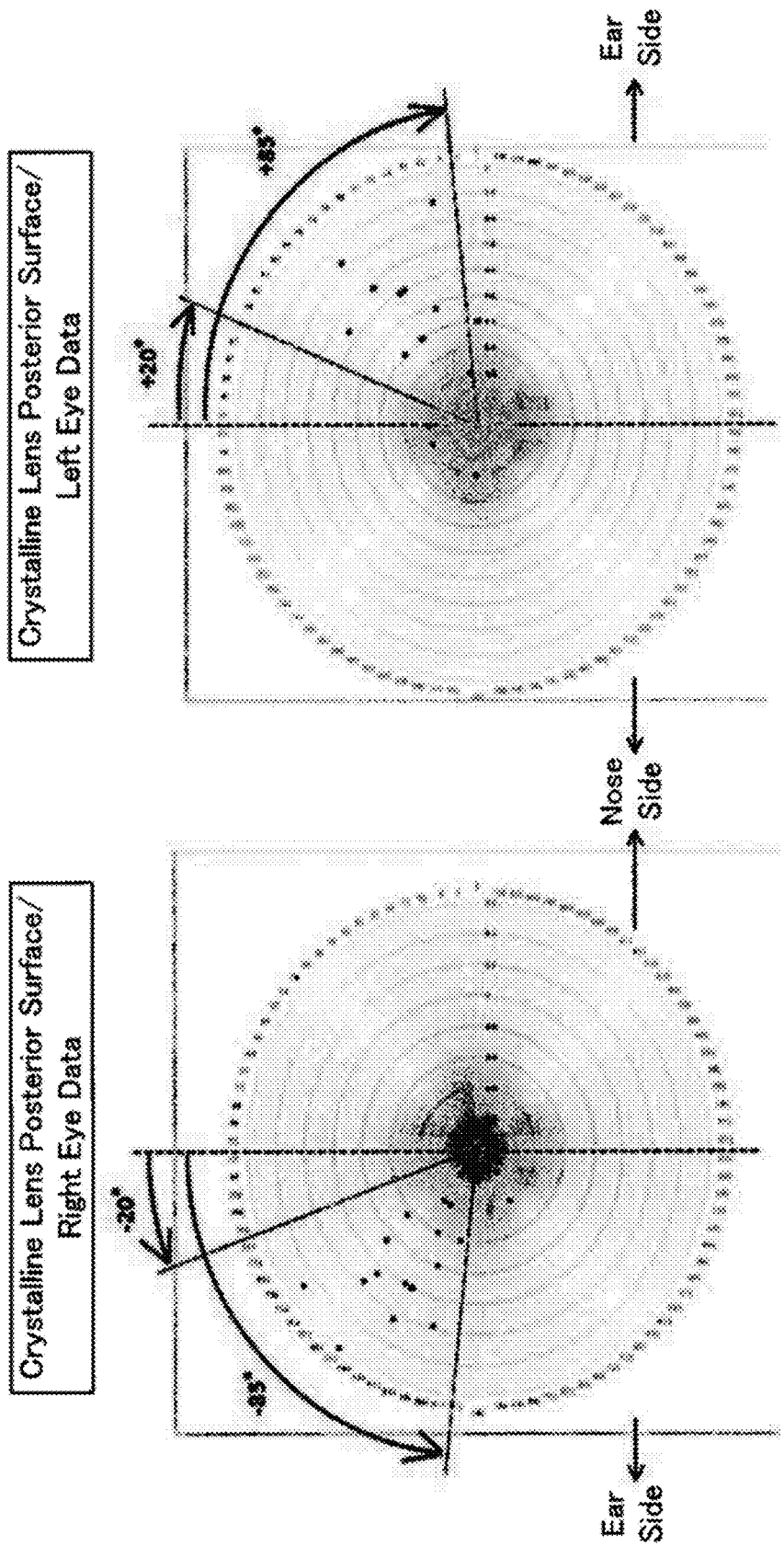
FIG. 8 shows experimental results when the positions of incidence are determined by experiments so as to maximize the intensity of reflected light from the posterior surface of the crystalline lens (right eye, left eye).

Experimental results on scanning of positions of incidence of light over the eyes of a plurality of persons will be described below. The positions of incidence include the incidence position of light when light reflected from the anterior surface position of the crystalline lens has the maximum intensity and the incidence position of light when light reflected from the posterior surface position of the crystalline lens has the maximum intensity. As shown in FIG. 7, on the anterior surface of the crystalline lens of a right eye, the incidence position of light where reflected light has the maximum intensity ranged from 20° to 85° clockwise, with a few exceptions, relative to a reference line extending upward from the cornea apex. On the anterior surface of the crystalline lens of a left eye, the incidence position of light where reflected light has the maximum intensity ranged from 20° to 85° counterclockwise, with a few exceptions, relative to the reference line. As shown in FIG. 8, on the posterior surface of the crystalline lens of the right eye, the incidence position of light where reflected light has the maximum intensity ranged from 20° to 85° counterclockwise, with a few exceptions, relative to the reference line. On the posterior surface of the crystalline lens of the left eye, the incidence position of light where reflected light has the maximum intensity ranged from 20° to 85° clockwise, with a few exceptions, relative to the reference line. Thus, the predetermined regions 108a and 108b are set as shown in FIG. 4, efficiently specifying the position where reflected light from the anterior surface of the crystalline lens is maximized and the position where reflected light from the posterior surface of the crystalline lens is maximized.

As has been discussed, in the ophthalmological device of the present embodiment, the incidence position of light emitted to the eye 100 is changed to specify an incidence position where the intensity of light reflected from the anterior and posterior surfaces of a target portion (e.g., the crystalline lens 104) of the eye 100 is maximized. Subsequently, the scanning line is set so as to pass through the specified incidence position, and then a measurement is conducted on the scanning line to calculate a dimension along the eye axis of the target portion. This can stably calculate a dimension along the eye axis of the target portion of the eye. Furthermore, when a search is conducted for positions of incidence where the intensity of reflected light is maximized, the search is conducted in the predetermined region that is likely to contain the positions of incidence. This can efficiently search for positions where the intensity of reflected light is maximized.

Moreover, in the ophthalmological device according to the present embodiment, the incidence position of light emitted to the eye 100 is moved using the convex lens 44 of the beam expander 40. Thus, light emitted to the eye 100 can be scanned at a high speed by driving the small convex lens 44. Moreover, by using the beam expander 40, a mechanism for scanning light can be manufactured at lower cost than in scanning of light with a galvanometer mirror or the like.

In the ophthalmological device of the present embodiment, the beam expander 40 has the function of adjusting a focus and the function of adjusting an incidence position. Thus, the beam expander 40 can collectively have the functions of driving (moving) the lens. This can reduce the number of components and the manufacturing cost.

Specific examples of the present teachings have been described in detail, however, these are mere exemplary indications and thus do not limit the scope of the claims. The art described in the claims include modifications and variations of the specific examples presented above.

For example, in the foregoing embodiment, the thickness and the depth of the anterior chamber of the crystalline lens are calculated. Dimensions may be calculated along the eye axis of other portions. Unlike in the foregoing embodiment, it is not always necessary to measure the thickness and the depth of the anterior chamber of the crystalline lens. Only the thickness of the crystalline lens or the depth of the anterior chamber may be measured. For example, if only the thickness of the crystalline lens is measured, light may be linearly scanned on a scanning line that is set to connect the first incidence position (the position where maximum light is reflected from the anterior surface of the crystalline lens) and the second incidence position (the position where maximum light is reflected from the posterior surface of the crystalline lens). Alternatively, if only the depth of the anterior chamber is measured, light may be linearly scanned on a scanning line set to connect the first incidence position and the cornea apex. With this configuration, a desired measurement can be made in a shorter time.

In the foregoing embodiment, the beam expander 40 includes the two convex lenses 42 and 44. The configuration is not limited to that of the embodiment. Various configurations (e.g., a combination of a concave lens and a convex lens and a combination of a convex lens and a concave lens) may be used. In other words, even in the case of a different configuration including a combination of a convex lens and a concave lens, the same functions (specifically, the functions of adjusting a focal position and an incidence position) as in the present embodiment can be obtained.

In the foregoing embodiment, the incidence position of light is changed using the beam expander 40. Other configurations may be adopted. For example, a lens disposed on an optical path may be two-dimensionally driven in a plane orthogonal to the optical path (optical axis).

In the foregoing embodiment, light is scanned in the predetermined regions 108a and 108b so as to calculate a dimension along the eye axis of a desired portion. If a dimension cannot be calculated along the eye axis of the desired portion only by scanning light in the predetermined regions 108a and 108b, a measurement may be conducted in a region (e.g., +85° to +135° and −85° to −135° (+ is a clockwise direction and − is a counterclockwise direction)) that is set in addition to the predetermined regions 108a and 108b. With this configuration, a small predetermined region can be set for an initial measurement, allowing measurements of, for example, a thickness on target portions of many persons with high efficiency (in a short time).

In the foregoing embodiment, the Fourier domain interferometer is used. A time domain interferometer may be used instead.

What is claimed is:

1. An ophthalmological device comprising:
   a light source;
   a measurement optical system configured to emit light from the light source into an eye to be examined and guide reflected light;
   a reference optical system configured to split light from the light source and generates reference light;
   a light receiving element configured to receive interfering light composed of the reflected light guided by the measurement optical system and the reference light generated by the reference optical system; and
   an arithmetic unit configured to calculate a dimension along an eye axis of a target portion of the eye from interfering light received by the light receiving element,
   the measurement optical system including:
   an incidence position changing member configured to change an incidence position of light emitted to the eye; and
   a driving unit configured to drive the incidence position changing member so as to scan at the incidence position of emitted light only in a predetermined region of the eye,
   wherein the predetermined region includes:
   a vertical reference line extended through a cornea apex viewed from a front of the eye such that the cornea apex is bifurcated by the vertical reference line and
   a straight line that extends from the vertical reference line that circumferentially moves over a predetermined angle range, of +20° to +85° in a clockwise direction or −20° to −85° in a counterclockwise direction with respect to the vertical reference line such that reflected light is identified in the predetermined angle range and used to identify a specific position in a target portion of the eye.

2. The ophthalmological device according to claim 1, wherein the arithmetic unit specifies a position of an anterior surface of the target portion and a position of a posterior surface of the target portion from interfering light received when light emitted to the eye is scanned in the predetermined region, and the arithmetic unit calculates a dimension along the eye axis of the target portion from the specified positions.

3. The ophthalmological device according to claim 2, wherein an incidence position at acquisition of interfering light for specifying the position of the anterior surface of the target portion is different from an incidence position at acquisition of interfering light for specifying the position of the posterior surface of the target portion.

4. The ophthalmological device according to claim 3, wherein when light emitted to the eye is scanned in the predetermined region, the arithmetic unit specifies a first incidence position where intensity of light reflected from the anterior surface of the target portion is maximized and a second incidence position where intensity of light reflected from the posterior surface of the target portion is maximized, the driving unit further drives the incidence position changing member such that light emitted to the eye is scanned on a scanning line set so as to pass through the first incidence position and the second incidence position, and the arithmetic unit calculates a dimension along the eye axis of the target portion from interfering light when light is scanned on the scanning line set so as to pass through the first incidence position and the second incidence position.

5. The ophthalmological device according to claim 4, wherein when the eye is viewed from the front, one of the first and second incidence positions is located on one side of a vertical line passing through the cornea apex of the eye, whereas the other incidence position is located on the other side of the vertical line.

6. The ophthalmological device according to claim 5, wherein the scanning line includes the cornea apex of the eye and has a first section connecting the cornea apex and the first incidence position and a second section connecting the cornea apex and the second incidence position.

7. The ophthalmological device according to claim 6, wherein the target portion is a depth of an anterior chamber from an anterior surface or a posterior surface of a cornea to an anterior surface of a crystalline lens and/or a thickness of the crystalline lens from the anterior surface to a posterior surface of the crystalline lens.

8. The ophthalmological device according to claim 7, wherein the incidence position changing member is a lens disposed on an optical axis of light emitted to the eye, and the driving unit moves the lens in a plane orthogonal to the optical axis.

9. The ophthalmological device according to claim 8, wherein the incidence position changing member is one of lenses constituting a beam expander disposed on the optical axis of light emitted to the eye.

10. The ophthalmological device according to claim 1, wherein when light emitted to the eye is scanned in the predetermined region, the arithmetic unit specifies a first incidence position where intensity of light reflected from the anterior surface of the target portion is maximized and a second incidence position where intensity of light reflected from the posterior surface of the target portion is maximized, the driving unit further drives the incidence position changing member such that light emitted to the eye is scanned on a scanning line set so as to pass through the first incidence position and the second incidence position, and the arithmetic unit calculates a dimension along the eye axis of the target portion from interfering light when light is scanned on the scanning line set so as to pass through the first incidence position and the second incidence position.

11. The ophthalmological device according to claim 1, wherein the incidence position changing member is a lens disposed on an optical axis of light emitted to the eye, and the driving unit moves the lens in a plane orthogonal to the optical axis.

* * * * *